(12) United States Patent
Olmarker et al.

(10) Patent No.: US 7,811,990 B2
(45) Date of Patent: *Oct. 12, 2010

(54) SOLUBLE CYTOKINE RECEPTORS TNF-α BLOCKING ANTIBODIES FOR TREATING SPINAL DISORDERS MEDIATED BY NUCLEUS PULPOSUS

(75) Inventors: Kjell Olmarker, Mölndal (SE); Bjorn Rydevik, Göthenburg (SE)

(73) Assignee: Sciaticon AB, Molndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/788,651

(22) Filed: Apr. 20, 2007

(65) Prior Publication Data

US 2008/0085274 A1    Apr. 10, 2008

Related U.S. Application Data

(63) Continuation-in-part of application No. 11/521,093, filed on Sep. 14, 2006, which is a continuation-in-part of application No. 10/225,237, filed on Aug. 22, 2002, now Pat. No. 7,115,557, which is a continuation-in-part of application No. 09/826,893, filed on Apr. 6, 2001, now abandoned, which is a continuation-in-part of application No. 09/743,852, filed as application No. PCT/SE99/01671 on Sep. 23, 1999, now Pat. No. 6,649,589.

(30) Foreign Application Priority Data

Sep. 25, 1998 (SE) .................................... 9803276
Oct. 29, 1998 (SE) .................................... 9803710

(51) Int. Cl.
A61K 38/16    (2006.01)
A61K 39/395   (2006.01)
C07K 14/435   (2006.01)

(52) U.S. Cl. .................. 514/12; 514/2; 424/130.1; 424/142.1; 530/350

(58) Field of Classification Search ................ None
See application file for complete search history.

(56) References Cited

U.S. PATENT DOCUMENTS

| | | |
|---|---|---|
| 4,666,897 A | 5/1987 | Golub et al. |
| 4,925,833 A | 5/1990 | McNamara et al. |
| 5,304,633 A | 4/1994 | Tomita et al. |
| 5,565,272 A | 10/1996 | Masui et al. |
| 5,565,425 A | 10/1996 | Yamamoto et al. |
| 5,574,022 A | 11/1996 | Roberts et al. |
| 5,602,157 A | 2/1997 | Christensen, IV |
| 5,605,690 A | 2/1997 | Jacobs et al. |
| 5,650,396 A | 7/1997 | Carlino et al. |
| 5,656,272 A | 8/1997 | Le et al. |
| 5,672,347 A | 9/1997 | Aggarwal et al. |
| 5,686,428 A | 11/1997 | Eriksson |
| 5,698,195 A | 12/1997 | Le |
| 5,703,092 A | 12/1997 | Xue et al. |
| 5,756,482 A | 5/1998 | Roberts et al. |
| 5,763,446 A | 6/1998 | Sadun et al. |
| 5,795,967 A | 8/1998 | Aggarwal et al. |
| 5,919,452 A | 7/1999 | Le |
| 5,962,481 A | 10/1999 | Levin et al. |
| 6,001,828 A | 12/1999 | Andrulis, Jr. et al. |
| 6,015,557 A | 1/2000 | Tobinick et al. |
| 6,177,077 B1 | 1/2001 | Tobinick |
| 6,180,355 B1 | 1/2001 | Alexander et al. |
| 6,277,966 B2 | 8/2001 | Kayane et al. |
| 6,277,969 B1 | 8/2001 | Le |
| 6,284,471 B1 | 9/2001 | Le |
| 6,319,910 B1 | 11/2001 | Amin et al. |
| 6,379,666 B1 | 4/2002 | Tobinick |
| 6,406,867 B1 | 6/2002 | Yu et al. |
| 6,419,934 B1 | 7/2002 | Tobinick |
| 6,419,944 B2 | 7/2002 | Tobinick |
| 6,423,321 B2 | 7/2002 | Tobinick |
| 6,428,787 B1 | 8/2002 | Tobinick |
| 6,471,961 B1 | 10/2002 | Tobinick |
| 6,537,549 B2 | 3/2003 | Tobinick |
| 6,623,736 B2 | 9/2003 | Tobinick |
| 6,635,250 B2 | 10/2003 | Olmarker et al. |
| 6,649,589 B1 | 11/2003 | Olmarker et al. |
| 6,790,444 B2 | 9/2004 | Le |
| 6,835,823 B2 | 12/2004 | Le |
| 6,982,089 B2 | 1/2006 | Tobinick |
| 6,991,791 B2 | 1/2006 | Le |

(Continued)

FOREIGN PATENT DOCUMENTS

DE    4 028 487    3/1992

(Continued)

OTHER PUBLICATIONS

U.S. Appl. No. 09/256,388, filed Feb. 24, 1999.

(Continued)

*Primary Examiner*—Christine J Saoud
*Assistant Examiner*—Jon M Lockard
(74) *Attorney, Agent, or Firm*—Fish & Richardson P.C.

(57) ABSTRACT

Described herein are methods and compositions for the treatment of spinal disorders mediated by nucleus pulposus. The compositions can include a soluble cytokine receptor and/or a TNF-α blocking antibody.

51 Claims, No Drawings

U.S. PATENT DOCUMENTS

| | | | |
|---|---|---|---|
| 7,070,775 | B2 | 7/2006 | Le |
| 7,101,674 | B2 | 9/2006 | Le |
| 7,115,557 | B2 | 10/2006 | Olmarker |
| 7,128,907 | B2 | 10/2006 | Le |
| 7,128,908 | B2 | 10/2006 | Le |
| 7,135,178 | B2 | 11/2006 | Le |
| 7,135,179 | B2 | 11/2006 | Le |
| 7,138,118 | B2 | 11/2006 | Le |
| 7,160,542 | B2 | 1/2007 | Le |
| 7,160,543 | B2 | 1/2007 | Le |
| 7,160,995 | B2 | 1/2007 | Le |
| 7,166,284 | B2 | 1/2007 | Le |
| 7,169,386 | B1 | 1/2007 | Le |
| 7,169,388 | B2 | 1/2007 | Le |
| 7,179,466 | B2 | 2/2007 | Le |
| 7,179,893 | B2 | 2/2007 | Le |
| 7,192,584 | B2 | 3/2007 | Le |
| 7,204,985 | B2 | 4/2007 | Le |
| 7,214,376 | B2 | 5/2007 | Le |
| 7,214,658 | B2 | 5/2007 | Tobinick |
| 7,223,396 | B2 | 5/2007 | Le |
| 7,226,250 | B2 | 6/2007 | Gatton |
| 7,226,593 | B2 | 6/2007 | Le |
| 7,227,003 | B2 | 6/2007 | Le |
| 7,252,823 | B2 | 8/2007 | Le |
| 7,276,239 | B2 | 10/2007 | Le |
| 7,335,358 | B2 | 2/2008 | Le |
| 7,374,761 | B2 | 5/2008 | Le |
| 7,404,955 | B2 | 7/2008 | Le |
| 7,416,729 | B2 | 8/2008 | Le |
| 7,425,330 | B2 | 9/2008 | Le |
| 2001/0027175 | A1 | 10/2001 | Olmarker |
| 2001/0053764 | A1 | 12/2001 | Sims |
| 2001/0055594 | A1 | 12/2001 | Olmarker |
| 2002/0131954 | A1 | 9/2002 | Tobinick |
| 2002/0132307 | A1 | 9/2002 | Le |
| 2002/0146419 | A1 | 10/2002 | Le |
| 2003/0007972 | A1 | 1/2003 | Tobinick |
| 2003/0113318 | A1 | 6/2003 | Tobinick |
| 2003/0133935 | A1 | 7/2003 | Le |
| 2003/0147891 | A1 | 8/2003 | Le |
| 2003/0176332 | A1 | 9/2003 | Olmarker |
| 2003/0180299 | A1 | 9/2003 | Le |
| 2003/0185826 | A1 | 10/2003 | Tobinick |
| 2003/0204066 | A1 | 10/2003 | Le |
| 2004/0115200 | A1 | 6/2004 | Le |
| 2005/0074454 | A1 | 4/2005 | Le |
| 2005/0220971 | A1 | 10/2005 | Coburn |
| 2005/0249735 | A1 | 11/2005 | Le |
| 2005/0255104 | A1 | 11/2005 | Le |
| 2005/0260201 | A1 | 11/2005 | Le |
| 2006/0018907 | A1 | 1/2006 | Le |
| 2006/0051381 | A1 | 3/2006 | Tobinick |
| 2006/0246073 | A1 | 11/2006 | Knight |
| 2007/0104711 | A1 | 5/2007 | Olmarker |
| 2007/0196373 | A1 | 8/2007 | Le |
| 2007/0196375 | A1 | 8/2007 | Tobinick |
| 2007/0298040 | A1 | 12/2007 | Le |
| 2008/0019964 | A1 | 1/2008 | Olmarker |
| 2008/0025976 | A1 | 1/2008 | Le |
| 2009/0022718 | A1 | 1/2009 | Le |

FOREIGN PATENT DOCUMENTS

| | | |
|---|---|---|
| DE | 4 219 626 | 12/1993 |
| JP | 07-145196 | 6/1995 |
| JP | 07-274970 | 10/1995 |
| JP | 07-309771 | 11/1995 |
| JP | 08-040925 | 2/1996 |
| JP | 08-073499 | 3/1996 |
| JP | 08-143468 | 6/1996 |
| JP | 09-165342 | 6/1997 |
| SE | 9803276-6 | 9/1998 |
| SE | 9803710-4 | 10/1998 |
| SE | 9803710-4 | 3/2000 |
| SE | 0200667-4 | 3/2002 |
| WO | WO 95/05363 | 2/1995 |
| WO | WO 97/06158 | 2/1997 |
| WO | WO 97/36871 | 10/1997 |
| WO | WO 98/05357 | 2/1998 |
| WO | WO 98/06424 | 2/1998 |
| WO | WO 98/06425 | 2/1998 |
| WO | WO 98/24766 | 6/1998 |
| WO | WO 98/34919 | 8/1998 |
| WO | WO 00/01730 | 1/2000 |
| WO | WO 00/18409 | 4/2000 |
| WO | WO 00/18909 | 4/2000 |
| WO | WO 00/22666 | 4/2000 |
| WO | WO 00/50079 | 8/2000 |
| WO | WO 00/75659 | 12/2000 |
| WO | WO 01/49321 | 7/2001 |
| WO | WO 01/87328 | 11/2001 |
| WO | WO 02/080893 | 10/2002 |
| WO | WO 03/073981 | 9/2003 |
| WO | WO 2004/032718 | 4/2004 |

OTHER PUBLICATIONS

U.S. Appl. No. 09/980,784, filed Jan. 8, 2002.
U.S. Appl. No. 11/788,651, filed Apr. 20, 2007.
U.S. Appl. No. 60/585,735, filed Jul. 6, 2004.
U.S. Appl. No. 60/760,236, filed Jan. 18, 2006.
U.S. Appl. No. 60/738,331, filed Nov. 18, 2005.
Amin et al., "A novel mechanism of action of tetracyclines: Effects on nitric oxide synthases," *Proc. Natl. Acad. Sci. USA*, 1996, 93:14014-14019.
Aoki et al., "Local Application of Disc-Related Cytokines on Spinal Nerve Roots," *Spine*, 2002, 27(15):1614-1617.
Arai et al., "Indomethacin blocks the nucleus pulposus-induced effects on nerve root function. An experimental study in dogs with assessment of nerve conduction and blood flow following experimental disc herniation," *Eur. Spine J.*, 2004, 13(8):691-694.
Baumgartner et al., "Constitutive and Inducible Mechanisms for Synthesis and Release of Cytokines in Immune Cell Lines," *J. Immunol.*, 1996, 157:4087-4093.
Bidani and Heming, "Effects of Lidocaine on Cytosolic pH Regulation and Stimulus-Induced Effector Functions in Alveolar Macrophages," *Lung*, 1997, 175:349-361.
Black et al., "A metalloproteinase disintegrin that releases tumour-necrosis factor-α from cells," *Nature*, 1997, 385:729-733.
Bluthé et al., "Interleukin-1 mediates behavioural but not metabolic effects of tumor necrosis factor α in mice," *Eur. J. Pharmacol.*, 1991, 209:281-283.
Boden et al., "Abnormal Magnetic-Resonance Scans of the Lumbar Spine in Asymptomatic Subjects. A prospective investigation," *J. Bone Joint Surg.*, 1990, 72A(3):403-408.
Boos et al., "1995 Volvo Award in Clinical Sciences. The Diagnostic Accuracy of Magnetic Resonance Imaging, Work Perception, and Psychosocial Factors in Identifying Symptomatic Disc Herniations," *Spine*, 1995, 20(24):2613-2625.
Boos et al., "Tissue Characterization of Symptomatic and Asymptomatic Disc Herniations by Quantitative Magnetic Resonance Imaging," *J. Orthop. Res.*, 1997, 15:141-149.
Bourrie et al., "Enhancement of endotoxin-induced interleukin-10 production by SR 31747A, a sigma ligand," *Eur. J. Immunol.*, 1995, 25:2882-2887.
Brattsand and Linden, "Cytokine modulation by glucocorticoids: mechanisms and actions in cellular studies," *Aliment Pharmacol. Ther.*, 1996, 10(suppl 2):81-90.
Brisby et al., "Proinflammatory cytokines in cerebrospinal fluid and serum in patients with disc herniation and sciatica," *Eur. Spine J.*, 2002, 11:62-66.
Brisby et al., "Inflammation in disc herniation may be a response to nucleus pulposus cell cytokine production and not primary infiltration of inflammatory cells," *45th Annual Meeting Orthopaedic Research Society*, Feb. 1-4, 1999, Anaheim, CA, 1 page.

Buck and Cooperman, "Single Protein Omission Reconstitution Studies of Tetracycline Binding to the 30S Subunit of *Escherichia coli* Ribosomes," *Biochemistry*, 1990, 29(22):5374-5379.

Burke et al., "Intervertebral discs which cause low back pain secrete high levels of proinflammatory mediators," *J. Bone Joint Surg. Br.*, 2002, 84:196-201.

Burke et al., "Spontaneous Production of Monocyte Chemoattractant Protein-1 and Interleukin-8 by the Human Lumbar Intervertebral Disc," *Spine*, 2002, 27(13):1402-1407.

Byröd et al., "A Rapid Transport Route Between the Epidural Space and the Intraneural Capillaries of the Nerve Roots," *Spine*, 1995, 20(2):138-143.

Byröd et al., "Methylprednisolone Reduces the Early Vascular Permeability Increase in Spinal Nerve Roots Induced by Epidural Nucleus Pulposus Application," *J. Orthop. Res.*, 1987, 18:983-987.

Chao et al., "Interleukin-1 and Tumor Necrosis Factor-α Synergistically Mediate Neurotoxicity: Involvement of Nitric Oxide and of *N*-Methyl-D-aspartate Receptors," *Brain Behav. Immun.*, 1995, 9:355-365.

Chapple et al., "Structure-Function Relationship of Antibacterial Synthetic Peptides Homologous to a Helical Surface Region on Human Lactoferrin against *Escherichia coli* Seroytpe O111," *Infection and Immunity*, 1998, 66(6):2434-2440.

Chin et al., "Etanercept (Enbrel®) therapy for chronic inflammatory demyelinating polyneuropathy," *J. Neurol. Sci.*, 2003, 210:19-21.

Cornefjord et al., "Nucleus pulposus-induced nerve root injury: effects of diclofenac and ketoprofen," *Eur. Spine J.*, 2002, 11:57-61.

Crickmore and Salmond, "The *Escherichia coli* heat shock regulatory gene is immediately downstream of a cell division operon: the *fam* mutation is allelic with *rpoH*," *Mol. Gen. Genet.*, 1986, 205:535-539.

Dawson et al., "Cyclosporin A inhibits the in vivo production of interleukin-1β and tumour necrosis factor α, but not interleukin-6, by a T-cell-independent mechanism," *Cytokine*, 1996, 8(12):882-888.

DeLeo et al., "Cytokine and growth factor immunohistochemical spinal profiles in two animal models of mononeuropathy," *Brain Res.*, 1997, 759:50-57.

Dhainaut et al., "CDP571, a humanized antibody to human tumor necrosis factor-α: Safety, pharmacokinetics, immune response, and influence of the antibody on cytokine concentrations in patients with septic shock," *Crit. Care Med.*, 1995, 23(9):1461-1469.

Dick et al., "Neutralizing TNF-alpha Activity Modulates T-cell Phenotype and Function in Experimental Autoimmune Uveoretinitis," *J. Autoimmunity*, 1998, 11(3):255-264.

"Development of Enbrel® (etanercept)," http://www.enbrel.com/rheumatology/enbrel-rhcpabout-devel.jsp, printed Oct. 19, 2005, 2 pages.

Gadient et al., "Interleukin-1 β and tumor necrosis factor-α synergistically stimulate nerve growth factor (NGF) release from cultured rat astrocytes," *Neurosci. Lett.*, 1990, 117:335-340.

García-Vicuña et al., "Prevention of cytokine-induced changes in leukocyte adhesion receptors by nonsteroidal antiinflammatory drugs from the oxicam family," *Arthritis Rheum.*, 1997, 40:143-153.

Gearing et al., "Processing of tumour necrosis factor-α precursor by metalloproteinases," *Nature*, 1994, 370:555-557.

Gelderd et al., "The Effects of Interleukin-1 Receptor Antagonist Protein (IRAP) Infusion Following Spinal Cord Transection in Rats," *Mol. Chem. Neuropathol.*, 1996, 27(2):167-183.

Gill and Salmond, "The identification of the *Escherichia coli ftsY* gene product: an unusual protein," *Mol. Microbiol.*, 1990, 4(4):575-583.

Goetzl et al., "Matrix Metalloproteinases in Immunity," *J. Immunol.*, 1996, 156:1-4.

Gonzalez et al., "Long-term effect of nonsteroidal anti-inflammatory drugs on the production of cytokines and other inflammatory mediators by blood cells of patients with osteoarthritis," *Agents Actions*, 1994, 41:171-178.

Hartung et al., "Inflammatory mediators in demyelinating disorders of the CNS and PNS," *J. Neuroimmunol.*, 1992, 40:197-210.

Hattori et al., "Tumor necrosis factor is markedly synergistic with interleukin I and interferon-γ in stimulating the production of nerve growth factor in fibroblasts," *FEBS Lett.*, 1994, 340:177-180.

Herman et al., "Nonsteroidal Antiinflammatory Drug Modulation of Prosthesis Pseudomembrane Induced Bone Resorption," *J. Rheumatol.*, 1994, 21:338-343.

Homma et al., "A comparison of chronic pain behavior following local application of tumor necrosis factor α to the normal and mechanically compressed lumbar ganglia in the rat," *Pain*, 2002, 95:239-246.

Igarashi et al., "2000 Volvo Award Winner in Basic Science Studies: Exogenous Tumor Necrosis Factor-Alpha Mimics Nucleus Pulposus-Induced Neuropathology. Molecular, Histologic, and Behavioral Comparisons in Rats," *Spine*, 2000, 25(23):2975-2980.

Iwabuchi et al., "Effects of Anulus Fibrosus and Experimentally Degenerated Nucleus Pulposus on Nerve Root Conduction Velocity," *Spine*, 2001, 26(15):1651-1655.

Iwamoto and Takeda, "Possible cytotoxic mechanisms of TNF in vitro," *Hum. Cell.*, 1990, 3:107-112 (English summary attached).

Jeanjean et al., "Interleukin-1β induces long-term increase of axonally transported opiate receptors and substance P," *Neuroscience*, 1995, 68(1):151-157.

Jurd et al., "Endothelial cell activation in cutaneous vasculitis," *Clin. Exp. Dermatol.*, 1996, 21:28-32.

Karppinen et al., "Treatment of Sciatica with Infliximab, a monoclonal humanised chimaeric antibody against TNF-α," *J. Bone Joint Surg.*, 2004, 86B(suppl 3):341-342, Abstract 03057.

Karppinen et al., "Tumor Necrosis Factor-α Monoclonal Antibody, Infliximab, Used to Manage Severe Sciatica," *Spine*, 2003, 28(8):750-754.

Kawakami et al., "mRNA Expression of Interleukins, Phospholipase $A_2$, and Nitric Oxide Synthase in the Nerve Root and Dorsal Root Ganglion Induced by Autologous Nucleus Pulposus in the Rat," *J. Orthopaedic Res.*, 1999, 17:941-946.

Kawakami et al., "Pathomechanism of Pain-Related Behavior Produced by Allografts of Intervertebral Disc in the Rat," *Spine*, 1996, 21(18):2101-2107.

Kayama et al., "Incision of the Anulus Fibrosus Induces Nerve Root Morphologic, Vascular, and Functional Changes. An experimental study," *Spine*, 1996, 21(22):2539-2543.

Kayama et al., "Cultured, Autologous Nucleus Pulposus Cells Induce Functional Changes in Spinal Nerve Roots," *Spine*, 1998, 23(20):2155-2158.

Kloppenburg et al., "The Tetracycline Derivative Minocycline Differentially Affects Cytokine Production by Monocytes and T Lymphocytes," *Antimicrob. Agents Chemother.*, 1996, 40(4):934-940.

Kloppenburg et al., "The influence of tetracyclines on T cell activation," *Clin. Exp. Immunol.*, 1995, 102:635-641.

Klusman and Schwab, "Effects of pro-inflammatory cytokines in experimental spinal cord injury," *Brain Res.*, 1997, 762:173-184.

"The body's own toxoids help in therapy," Dec. 12, 1999, http://www.rp-online.de/news/wissenschaft/1999-1230/bandscheibenvorfall.html, translation included.

Köller et al., "Immunologically induced electrophysiological dysfunction: Implications for inflammatory diseases of the CNS and PNS," *Prog. Neurobiol.*, 1997, 52:1-26.

Kraemer et al., "Lumbar epidural perineural injection: a new technique," *Eur. Spine J.*, 1997, 6(5):357-361.

Lamster et al., "The effect of tetracycline fiber therapy on β-glucuronidase and interleukin-1β in crevicular fluid," *J. Clin. Periodontol.*, 1996, 23:816-822.

Liberski et al., "Further ultrastructural studies of lesions induced in the optic nerve by Tumor necrosis factor alpha (TNF-α): a comparison with experimental Creutzfeldt-Jakob disease," *Acta Neurobiol. Exp.*, 1994, 54:209-218.

Lin et al., "An immunohistochemical study of TNF-α in optic nerves from AIDS patients," *Curr. Eye Res.*, 1997, 16:1064-1068.

Liu et al., "Increased Sensitivity of Sensory Neurons to Tumor Necrosis Factor α in Rats with Chronic Compression of the Lumbar Ganglia," *J. Neurophysiol.*, 2002, 88:1393-1399.

Lorenz and Kalden, "Biological Agents in Rheumatoid Arthritis," *BioDrugs*, 1998, 9(4):303-324.

Madigan et al., "Tumor necrosis factor-alpha (TNF-α)-induced optic neuropathy in rabbits," *Neurol. Res.*, 1996, 18:176-184.

Malcangio et al., "Effect of interleukin-1β on the release of substance P from rat isolated spinal cord," *Eur. J. Pharmacol.*, 1996, 299:113-118.

Matsumori et al., "Amiodarone Inhibits Production of Tumor Necrosis Factor-α by Human Mononuclear Cells. A Possible Mechanism for its Effect in Heart Failure," *Circulation*, 1997, 96:1386-1389.

Milano et al., "Intraperitoneal Injection of Tetracyclines Protects Mice from Lethal Endotoxemia Downregulating Inducible Nitric Oxide Synthase in Various Organs and Cytokine and Nitrate Secretion in Blood," *Antimicrob. Agents Chemother.*, 1997, 41:117-121.

Mixter and Barr, "Rupture of the intervertebral disc with involvement of the spinal canal," *New Eng. Surg. Soc.*, 1934, 211(6):210-215.

Moelling, "DNA for genetic vaccination and therapy," *Cytokines Cell. Mol. Ther.*, 1997, 3(2):127-136.

Nawroth et al., "Tumor necrosis factor/cachectin-induced intravascular fibrin formation in meth A fibrosarcomas," *J. Exp. Med.*, 1988, 168:637-647.

Nishi et al., "DNA Sequence and Complementation Analysis of a Mutation in the *rplX* Gene from *Escherichia coli* Leading to Loss of Ribosomal Protein L24," *J. Bacteriol.*, 1985, 163(3):890-894.

Odell et al., "Antibacterial activity of peptides homologous to a loop region in human lactoferrin," *FEBS Lett.*, 1996, 382:175-178.

Oka et al., "Intracerebroventricular Injection of Tumor Necrosis Factor-α Induces Thermal Hyperalgesia in Rats," *Neuroimmunomodulation*, 1996, 3:135-140.

Olmarker et al., "Inflammatogenic Properties of Nucleus Pulposus," *Spine*, 1995, 20(6):665-669.

Olmarker et al., "The Effects of Normal, Frozen, and Hyaluronidase-Digested Nucleus Pulposus on Nerve Root Structure and Function," *Spine*, 1997, 22(5):471-476.

Olmarker et al., "Effects of Methylprednisolone on Nucleus Pulposus-Induced Nerve Root Injury," *Spine*, 1994, 19(16):1803-1808.

Olmarker and Larsson, "Tumor Necrosis Factor α and Nucleus-Pulposus-Induced Nerve Root Injury," *Spine*, 1998, 23(23): 2538-2544.

Olmarker and Myers, "Pathogenesis of sciatic pain: role of herniated nucleus pulposus and deformation of spinal nerve root and dorsal root ganglion," *Pain*, 1998, 78(2):99-105.

Olmarker et al., "Ultrastructural Changes in Spinal Nerve Roots Induced by Autologous Nucleus Pulposus," *Spine*, 1996, 21(4):411-414.

Olmarker and Rydevik, "Selective Inhibition of Tumor Necrosis Factor-α Prevents Nucleus Pulposus-Induced Thrombus Formation, Intraneural Edema, and Reduction of Nerve Conduction Velocity. Possible Implications for Future Pharmacologic Treatment Strategies of Sciatica," *Spine*, 2001, 26(8):863-869.

Olmarker et al., "Autologous Nucleus Pulposus Induces Neurophysiologic and Histologic Changes in Porcine Cauda Equina Nerve Roots," *Spine*, 1993, 18(11):1425-1432.

Onda et al., "Exogenous Tumor Necrosis Factor-α Induces Abnormal Discharges in Rat Dorsal Horn Neurons," *Spine*, 2002, 27(15):1618-1624.

Otani et al., "Nucleus Pulposus-induced Nerve Root Injury: Relationship between Blood Flow and Motor Nerve Conduction Velocity," *Neurosurgery*, 1999, 45(3):614-620.

Pennica et al., "Cardiotrophin-1, a Cytokine Present in Embryonic Muscle, Supports Long-Term Survival of Spinal Motoneurons," *Neuron*, 1996, 17:63-74.

Person, "Dermatomyositis responding to pentoxifylline," *Br. J. Dermatol.*, 1995, 134(3):593.

Petrovich et al., "Pentoxifylline suppression of TNF-α mediated axonal degeneration in the rabbit optic nerve," *Neurol. Res.*, 1997, 19:551-554.

Pichler et al., "High IL-5 Production by Human Drug-Specific T Cell Clones," *Int. Arch. Allergy Immunol.*, 1997, 113:177-180.

Plata-Salaman et al., "Interleukin-1β enhances spinal cord blood flow after intrathecal administration in the normal rat," *Am. J. Physiol.*, 1995, 269:R1032-R1037.

Rand et al., "Murine Nucleus Pulposus-Derived Cells Secrete Interleukins-1-β, -6, and -10 and Granulocyte-Macrophage Colony-Stimulating Factor in Cell Culture," *Spine*, 1997, 22(22):2598-2601.

Redford et al., "Vascular changes and demyelination induced by the intraneural injection of tumour necrosis factor," *Brain*, 1995, 118:869-878.

Reinecke et al., "The Use of Interleukin-1-Receptor Antagonist (IL-1 ra) in the Treatment of the Lumbar Facet Syndrome," ISSLS, Abstracts 2000, Adelaide, Australia, Abstract 173.

Reinecke et al., "In vitro Transfer of Genes into Spinal Tissues," *Z. Orthop.*, 1997, 135(5):412-416 (English summary included).

Robache-Gallea et al., "Partial purification and characterization of a tumor necrosis factor-α converting activity," *Eur. J. Immunol.*, 1997, 27:1275-1282.

Rosendahl et al., "Identification and Characterization of a Pro-tumor Necrosis Factor-α-processing Enzyme from the ADAM Family of Zinc Metalloproteases," *J. Biol. Chem.*, 1997, 272(39):24588-24593.

Rost, "Twilight zone of protein sequence alignments," *Protein Engineering*, 1999, 12(2):85-94.

Rowin et al., "Etanercept treatment in corticosteroid-dependent myasthenia gravis," *Neurology*, 2004, 63:2390-2392.

Rydevik et al., "Effects of graded compression and nucleus pulposus on nerve tissue: an experimental study in rabbits," *Acta Orthop. Scand.*, 1983, 54:670-671.

Safieh-Garabedian et al., "Contribution of interleukin-1β to the inflammation-induced increase in nerve growth factor levels and inflammatory hyperalgesia," *Brit. J. Pharmacol.*, 1995, 115(7):1265-1275.

Safieh-Garabedian et al., "Involvement of Interleukin-1β, Nerve Growth Factor, and Prostaglandin-$E_2$ in the Hyperalgesia Induced by Intraplantar Injections of Low Doses of Thymulin," *Brain Behav. Immun.*, 1997, 11(3):185-200.

Safieh-Garabedian et al., "Zinc Reduces the Hyperalgesia and Upregulation of NGF and IL-1β Produced by Peripheral Inflammation in the Rat," *Neuropharmacol.*, 1996, 35(5):599-603.

Said and Hontebeyrie-Joskowicz, "Nerve lesions induced by macrophage activation," *Res. Immunol.*, 1992, 143:589-599.

Schäfers et al., "Combined epineurial therapy with neutralizing antibodies to tumor necrosis factor-alpha and interleukin-1 receptor has an additive effect in reducing neuropathic pain in mice," *Neurosci. Lett.*, 2001, 310:113-116.

Schenk and Reiter, "Intrathecal cortison injection in lumbar disc problems," *Arch. Orthopadische Und Unfall-Chirurgie*, 1976, 85(1):21-31 (English abstract).

Schlumpf and Johr, "Acute lumbar disk displacement with nerve root compression. Indications for peridural steroid injection," *Schweizerische Rundschau Fur Medizin Praxis*, 1997, 86(8):292-295.

Seekamp et al., "Requirements for tumor necrosis factor-alpha and interleukin-1 in limb ischemia/reperfusion injury and associated lung injury," *Am. J. Pathol.*, 1993, 143(2):453-463.

Selmaj and Raine, "Tumor Necrosis Factor Mediates Myelin and Oligodendrocyte Damage In Vitro," *Ann. Neurol.*, 1988, 23:339-346.

Shapira et al., "Human Monocyte Response to Cementum Extracts From Periodontally Diseased Teeth: Effect of Conditioning With Tetracycline," *J. Periodontol.*, 1996, 67:682-687.

Shapira et al., "Tetracycline inhibits *Porphyromonas gingivalis* lipopolysaccharide-induced lesions in vivo and TNFα processing in vitro," *J. Periodont. Res.*, 1997, 32:183-188.

Sharief et al., "Circulating Tumor Necrosis Factor-α Correlates with Electrodiagnostic Abnormalities in Guillain-Barré Syndrome," *Ann. Neurol.*, 1997, 42:68-73.

Sharma et al., "Topical application of TNF-α antiserum attenuates spinal cord trauma induced edema formation, microvascular permeability disturbances and cell injury in the rat," *Acta Neurochir*, 2003, 86(suppl):1-7.

Shinmei et al., "The Role of Interleukin-1 on Proteoglycan Metabolism of Rabbit Annulus Fibrosus Cells Cultured In Vitro," *Spine*, 1988, 13(11):1284-1290.

Skouen et al., "Protein Markers in Cerebrospinal Fluid in Experimental Nerve Root Injury. A study of slow-onset chronic compression effects or the biochemical effects of nucleus pulposus on sacral nerve roots," *Spine*, 1999, 24(21):2195-2200.

Smith, "Microbial pathogen genomes-new strategies for identifying therapeutics and vaccine targets," *Tibtech*, 1996, 14:290-293.

Smith et al., "Cyclosporin A blocks induction of tumor necrosis factor-alpha in human B lymphocytes," *Biochem. Biophys. Res. Commun.*, 1994, 204:383-390.

Smolen et al., "Efficacy and safety of leflunomide compared with placebo and sulphasalazine in active rheumatoid arthritis: a double-blind, randomized, multicentre trial," *Lancet*, 1999, 353:259-266.

Sommer et al., "A metalloprotease-inhibitor reduces pain associated behavior in mice with experimental neuropathy," *Neurosci. Letters*, 1997, 237:45-48.

Sommer et al., "The effect of thalidomide treatment on vascular pathology and hyperalgesia caused by chronic constriction injury of rat nerve," *Pain*, 1998, 74:83-91.

Sommer et al., "Etanercept reduces hyperalgesia in experimental painful neuropathy," *J. Peripheral Nerve Syst.*, 2001, 6:67-72.

Sorkin et al., "Tumour necrosis factor-α induces ectopic activity in nociceptive primary afferent fibres," *Neuroscience*, 1997, 81:255-262.

Steinmeyer et al., "Pharmacological Effect of Tetracyclines on Proteoglycanases from Interleukin-1-Treated Articular Cartilage," *Biochem. Pharmacol.*, 1998, 55:93-100.

Stephens and Shapiro, "Bacterial protein secretion-a target for new antibiotics?" *Chem. Biol.*, 1997, 4(9):637-641.

Stoll et al., "Tumor necrosis factor-α in immune-mediated demyelination and Wallerian degeneration of the rat peripheral nervous system," *J. Neuroimmunol.*, 1993, 45:175-182.

Szlosarek and Balkwill, "Tumour necrosis factor α a potential target for the therapy of solid tumours," *Lancet Oncol.*, 2003, 4:565-573.

Takahashi et al., "Inflammatory Cytokines in the Herniated Disc of the Lumbar Spine," *Spine*, 1996, 21(2):218-224.

Takao et al., "Lidocaine attenuates hyperoxic lung injury in rabbits," *Acta Anaesthesiol. Scand.*, 1996, 40:318-325.

Teoh et al., "Steroid Inhibition of Cytokine-Mediated Vasodilation After Warm Heart Surgery," *Circulation*, 1995, 92(suppl 2):II-347-II-353.

Tobinick and Davoodifar, "Perispinal TNF-alpha inhibition for discogenic pain," *Swiss Med. Wkly.*, 2003, 133:170-177.

Tobinick and Davoodifar, "Efficacy of etanercept delivered by perispinal administration for chronic back and/or neck disc-related pain: a study of clinical observations in 143 patients," *Curr. Med. Res. Opin.*, 2004, 20(7):1075-1085.

Tobinick, "Targeted Etanercept for Discogenic Neck Pain: Uncontrolled, Open-Label Results in Two Adults," *Clin. Ther.*, 2003, 25:1211-1218.

Tobinick, "Targeted Etanercept for Treatment-Refractory Pain Due to Bone Metastasis: Two Case Reports," *Clin. Thera.*, 2003, 25(8):2279-2288.

Tsukamoto et al., "Suppressive effects of TNF-α on myelin formation in vitro," *Acta Neurol. Scand.*, 1995, 91:71-75.

van der Poll et al., "Tumor Necrosis Factor-α Induces Activation of Coagulation and Fibrinolysis in Baboons Through an Exclusive Effect on the p55 Receptor," *Blood*, 1996, 88(3):922-927.

Villarroya et al., "Myelin-induced experimental allergic encephalomyelitis in Lewis rats: tumor necrosis factor α levels in serum of cerebrospinal fluid Immunohistochemical expression in glial cells and macrophages of optic nerve and spinal cord," *J. Neuroimmunol.*, 1996, 64:55-61.

Wacnik et al., "Nociceptive Characteristics of Tumor Necrosis Factor-α in Naïve and Tumor-Bearing Mice," *Neuroscience*, 2005, 132:479-491.

Wagner and Myers, "Schwann cells produce tumor necrosis factor alpha: expression in injured noninjured nerves," *Neuroscience*, 1996, 73(3):625-629.

Wagner and Myers, "Endoneurial injection of TNF-α produces neuropathic pain behaviors," *NeuroReport*, 1996, 7:2897-2901.

Wang et al., "Production of tumor necrosis factor in spinal cord following traumatic injury in rats," *J. Neuroimmunol.*, 1996, 69:151-156.

Wasaki et al., "Preventive effect of cyclosporin A on experimentally induced acute liver injury in rats," *Liver*, 1997, 17:107-114.

Wehling, "Antizytokine gegen entzundung und schmerz (Anticytokines against inflamation and pain)," Orthopadische Nachrichten, 1998, p. 16, Biermann Verlag GmbH, Koln, Germany, http://www.arthrose-ischias.de/ftp/presse 2.pdf, translation included.

Wehling et al., "Epidural Injections with Interleukin-1-Receptor-Antagonist-Protein (IRAP) in Lumbar Radicular Compression: Pathophysiological Background, Safety and Clinical Results," *Int. Soc. Study Lumbar Spine*, 1998, p. 16.

Wehling et al., "Neurophysiologic Changes in Lumbar Nerve Root Inflammation in the Rat After Treatment with Cytokine Inhibitors: Evidence for a Role of Interleukin-1," *Spine*, 1996, 21(8):931-935.

Wehling et al., "The Effect of Cytokines on Regeneration of Compressed Nerve Roots and Transsected Peripheral Nerves," *Z. Orthop.*, 1993, 131:83-93 (English summary included).

Wehling et al., "The interaction between synovial cytokines and peripheral nerve function: a possible element in the development of radicular syndromes," *Z. Orthop.*, 1990, 128(5):442-446 (English summary included).

Wehling, "The Use of Cytokine Antagonists in the Treatment of Lumbar Radicular Compression: Pathophysiological Background, Safety and 3 Year Clinical Experience," *Abstr. Int. Soc. Study Lumbar Spine*, Adelaide, Australia, Apr. 9-13, 2000, Abstract 38.

Wehling et al., "Transfer of Genes to Chondrocytic Cells of the Lumbar Spine: Proposal for a Treatment Strategy of Spinal Disorders by Local Gene Therapy," *Spine*, 1997, 22(10):1092-1097.

Wehling, Wissenschaftliches programm (Scientific Program), Jun. 18, 1999, "Epidural injection with a new autologous interleukin-1 receptor-antagonist-protein (IL-1 ra) at radicular compression: pathophysiology, safety and clinical results," http://medweb.uni-muenster.de/institute/orth/versanstaltungen/99-06-18v.html, relevant portions translated.

Weilbach and Gold, "Disease Modifying Treatments for Multiple Sclerosis. What Is On The Horizon?" *CNS Drugs*, 1999, 11(2):133-157.

Weinblatt et al., "A trial of Etanercept, a recombinant tumor necrosis factor receptor: Fc fusion protein, in patients with rheumatoid arthritis receiving methotrexate," *N. Engl. J. Med.*, 1999, 340(4):253-259.

Wershil et al., "Dexamethasone Cyclosporin A Suppress Mast Cell-Leukocyte Cytokine Cascades by Multiple Mechanisms," *Int. Arch. Allergy Immunol.*, 1995, 107:323-324.

Wiesel et al., "1984 Volvo Award in Clinical Sciences. A Study of Computer-Assisted Tomography. I. The Incidence of Positive CAT Scans in an Asymptomatic Group of Patients," *Spine*, 1984, 9(6):549-551.

Willison and Tissot, "The *Escherichia coli efg* Gene and the *Rhodobacter capsulatus adgA* Gene Code for $NH_3$-Dependent NAD Synthetase," *J. Bacteriol.*, 1994, 176(11):3400-3402.

Woolf et al., "Cytokines, nerve growth factor and inflammatory hyperalgesia: the contribution of tumour necrosis factor α," *Br. J. Pharmacol.*, 1997, 121(3):417-424.

Wower et al., "Ribosomal Protein L27 Participates in both 50 S Subunit Assembly and the Peptidyl Transferase Reaction," *J. Biol. Chem.*, 1998, 273(31):19847-19852.

Yabuki et al., "Effects of Lidocaine on Nucleus Pulposus-Induced Nerve Root Injury," *Spine*, 1998, 23(22):2383-2390.

Yabuuchi et al., "Biphasic effects of intra intracerebroventricular interleukin-1 β on mechanical nociception in the rat," *Eur. J. Pharmacol.*, 1996, 300:59-65.

Zhu et al., "Cytokine Dichotomy in Peripheral Nervous System Influences the Outcome of Experimental Allergic Neuritis: Dynamics of mRNA Expression for IL-1β, IL-6, IL-10, IL-12, TNF-α, TNF-β, and Cytolysin," *Clin. Immunol. Immunopathol.*, 1997, 84:85-94.

Zanella et al., "Effect of Etanercept, a Tumor Necrosis Factor-Alpha Inhibitor, on Neuropathic Pain in the Rat Chronic Constriction Injury Model," *Spine*, 2008, 33(3):227-234.

U.S. Appl. No. 07/670,827, filed Mar. 18, 1991.
U.S. Appl. No. 07/853,606, filed Mar. 18, 1992.
U.S. Appl. No. 07/943,852, filed Sep. 11, 1992.
U.S. Appl. No. 08/010,406, filed Jan. 29, 1993.
U.S. Appl. No. 08/013,413, filed Feb. 2, 1993.
U.S. Appl. No. 08/570,674, filed Dec. 11, 1995.
U.S. Appl. No. 08/442,133, filed May 16, 1995.
U.S. Appl. No. 09/765,978, filed Jan. 18, 2001.
U.S. Appl. No. 09/766,536, filed Jan. 18, 2001.

U.S. Appl. No. 10/043,450, filed Jan. 10, 2002.
U.S. Appl. No. 10/957,543, filed Sep. 30, 2004.
U.S. Appl. No. 12/346,737, filed Dec. 30, 2008.
U.S. Appl. No. 12/344,452, filed Dec. 26, 2008.
U.S. Appl. No. 12/344,437, filed Dec. 26, 2008.
Mohler et al., "Soluble tumor necrosis factor (TNF) receptors are effective therapeutic agents in lethal endotoxemia and function simultaneously as both TNF carriers and TNF antagonists," *J. Immunol.*, 1993, 151(3); pp. 1548-1561.
Muto et al., "Treatment of Herniated Lumbar Disc by Intradiscal and Intraforaminal Oxygen-Ozone ($O_2$-$O_3$) Injection," *J. Neuroradiol.*, 2004, 31; pp. 183-189.
Olmarker, Summary of U.S. Appl. No. 09/760,811, filed Jan. 17, 2001 (10 pages).
Scallon, et al, "Functional Comparisons of Different Tumour Necrosis Factor Receptor/IgG Fusion Proteins," *Cytokine*, 1995, 7(8), pp. 759-770.
Scallon, et al., "Binding and Functional Comparisons of Two Types of Tumor Necrosis Factor Antagonists," *The Journal of Pharmcology and Experimental Therapeutics*, 2002, 301(2); pp. 418-426.
Tartaglia, et al., "The two different receptors for tumor necrosis factor mediate distinct cellular responses," *Proc. Natl. Acad. Sci*, 1991, vol. 88, pp. 9292-9296.
Tracey, et al., "Tumor necrosis factor antagonist mechanisms of action: A comprehensive review," *Pharmacology & Therapeutics*, 2008, vol. 117; pp. 244-279.
Krakauer et al., "Doxycycline Is Anti-Inflammatory and Inhibits Staphylococcal Exotoxin-Induced Cytokines and Chemokines," *Antimicrob. Agents and Chemotherapy*, Nov. 2003, vol. 47(11): pp. 3630-3633
*Curriculum Vitae* of Mark L. Heaney, M.D., Ph.D., Memorial Sloan-Kettering Cancer Center and Weill Medical College of Cornell University Required Format for *Curriculum Vitae* and Bibliography, May 11, 2009 (11 pages).
Development of ENBREL[www.enbrel.com/hcp/enbrel-development.jsp], printed on Sep. 6, 2009 (3 pages).
Enbrel® (etanercept) For Subcutaneous Injection (2 pages) (2000).

Evans, et al., "Protective Effect of 55- but not 75-kD Soluble Tumor Necrosis Factor Receptor-Immunoglobulin G Fusion Proteins in an Animal Model of Gram-negative Sepsis," J. *Exp. Med.*, 1994, 180: 2173-2179.
Furst et al., "Intravenous Human Recombinant Tumor Necrosis Factor Receptor p55-Fc IgG1 Fusion Protein, Ro 45-2081 (Lenercept): Results of a Dose-Finding Study in Rheumatoid Arthritis," *The J. Of Rheumatology*, 2003, 30: 2123-2126.
Mohler et al., "Soluble tumor necrosis factor (TNF) receptors are effective therapeutic agents in lethal endotoxemia and function simultaneously as both TNF carriers and TNF antagonists," *J. Immunol.*, 1993, 151(3); pp. 1548-1561.
Olmarker, et al., "Tumor Necrosis Factor α and Nucleus-Pulposus-Induced Nerve Root Injury," *Spine*, 1998, 23(23): 2538-2544.
Scallon, et al., "Binding and Functional Comparisons of Two Types of Tumor Necrosis Factor Antagonists," *The Journal of Pharmcology and Experimental Therapeutics*, 2002, 301(2); pp. 418-426.
The Lenercept Multiple Sclerosis Study Group and The University of British Columbia MS/MRI Analysis Group, "TNF neutralization in MS: Results of a randomized, placebo-controlled multicenter study," *Neurology*, 1999, 53(3): 457-465.
Notice of Allowance mailed Oct. 30, 2009; Canada Patent Application No. 2,342,200.
Office Action mailed Aug. 3, 2009; EP Application No. 07009705.0.
Office Action mailed Nov. 20, 2009; Japan Application No. 2000-571927.
Goupille, et al., "The Role of Inflammation in Disk Herniation—Associated Radiculopathy," *Semin. Arthritis Rheum.*, 1998, 28(1): 60-71.
Onrust, et al "Infiximab: A Review of its Use in Crohn's Disease and Rheumatoid Arthritis," *BioDrugs*, 1998, 10(5): 397-422.
Sorbera, "Etanercept, Antiarthritic TNF-α Antagonist," *Drugs of the Future*, 1998, 23(9): 951-954.
Weithmann et al., "Effects of tiaprofenic acid on urinary pyridinium crosslinks in adjuvant arthritic rats: Comparison with doxycycline," *Inflamm. Res.*, 1997, 46: 246-252.

SOLUBLE CYTOKINE RECEPTORS TNF-α BLOCKING ANTIBODIES FOR TREATING SPINAL DISORDERS MEDIATED BY NUCLEUS PULPOSUS

This application is a continuation-in-part of U.S. patent application Ser. No. 11/521,093, filed on Sep. 14, 2006, which is a continuation-in-part of U.S. patent application Ser. No. 10/225,237, filed on Aug. 22, 2002, now U.S. Pat. 7,115,557, which is a continuation in part of Ser. No. 09/826,893 filed on Apr. 6, 2001, now abandoned, which is a continuation-in-part of U.S. patent application Ser. No. 09/743,852 filed on Jan. 17, 2001, now U.S. Pat. No. 6,649,589, which was a National Stage filing under 35 U.S.C. § 371 of International Application No. PCT/SE99/01671 filed on Sep. 23, 1999 which was published in English on Apr. 6, 2000 and claims benefit of Swedish Application Nos. 9803276-6 and 9803710-4 filed respectively on Sep. 25, 1998 and Oct. 29, 1998. These applications are herein incorporated by reference in their entirety for all purposes.

TECHNICAL FIELD

The present invention relates to the use of a TNF-α inhibitor in the preparation of pharmaceutical compositions for the treatment of nerve root injury, as well as a method for treating nerve root injury.

The object of the present invention is to obtain a possibility to treat nerve root injury, which may turn up as sciatica, by blocking disk related cytokines.

BACKGROUND OF THE INVENTION

Disk herniation is a troublesome disorder, which causes great pain and lost of motility, and thereby loss of productive life. Disk herniation will cause trouble to a varying degree, and the pain may last for a month or in sever cases up to 6 months. Beside the pain sciatica may cause sever handicapping problems, as the one suffering therefrom will feel crippled thereof.

U.S. Pat. No. 5,703,092 discloses the use of hydroxamic acid compounds and carbocyclic acids as metalloproteinase and TNF inhibitors, and in particular in treatment of arthritis and other related inflammatory diseases. No use of these compounds for the treatment of nerve root injuries is disclosed or hinted at.

U.S. Pat. No. 4,925,833 discloses the use of tetracyclines to enhance bone protein synthesis, and treatment of osteoporosis.

U.S. Pat. No. 4,666,897 discloses inhibition of mammalian collagenolytic enzymes by tetracyclines. The collagenolytic activity is manifested by excessive bone resorption, periodontal disease, rheumatoid arthritis, ulceration of cornea, or resorption of skin or other connective tissue collagen.

Neither of these latter two documents mentions nerve root injury or the treatment thereof. It has been noted that cytokines from nucleus pulposus-cells such as TNF-α, interleukin 1-β and interferon-γ and others cause structural and functional damages on closely situated nerves in connection with e.g., a disk herniation. Furthermore the nerve becomes sensitized by these substances to produce pain when they are mechanically deformed.

DESCRIPTION OF THE PRESENT INVENTION

It has now surprisingly been shown possible to be able to treat nerve root injuries, or at least alleviate the symptoms of nerve root injuries by using a pharmaceutical composition comprising an therapeutically active amount of a metalloproteinase inhibitor, tetracyclines including chemically modified tetracyclines, quinolones, corticosteroids, cyclosporine, thalidomide, lazaroides, pentoxyphylline, hydroxamic acid derivatives, napthopyrans, soluble cytokine receptors, amrinone, pimobendan, vesnarinone, phosphodiesterase III inhibitors, and melatonin in the form of bases or addition salts together with a pharmaceutically acceptable carrier.

The therapeutically effective amount is a dosage normally used when using such compounds for other therapeutic uses. Many of these drugs are commercially known registered drugs.

Compounds that possess this activity are tetracyclines, such as tetracycline, doxycycline, lymecycline, oxytetracycline, minocycline, and chemically modified tetracyclines dedimethylaminotetracycline, hydroxamic acid compounds, carbocyclic acids and derivatives, cyclosporine methylpredinsolone, thalidomide, lazaroides, pentoxyphylline, napthopyrans, soluble cytokine receptors, amrinone, pimobendan, vesnarinone, phosphodiesterase III inhibitors, melatonin, norfloxacine, ofloxacine, ciprofloxacine, gatifloxacine, pefloxacine, lomefloxacine, and temafloxacine. These can be present as bases or in the form of addition salts, whichever possesses the best pharmaceutical effect, and best property to be brought into a pharmaceutical suitable composition.

Further, the active component comprises a substance inhibiting a compound trigged by the release of TNF-α, such as interferon-gamma, interleukin-1, and nitrogen oxide (NO) in the form of base or addition salts.

The invention further relates to a method for inhibiting the symptoms of nerve root injury. The effect of doxycycline has been studied and the methods used and results obtained are disclosed below.

EXAMPLE

Study Design

The effects of nucleus pulposus and various treatments to block TNF-α activity were evaluated in an experimental set-up using immunohistochemistry and nerve conduction velocity recordings.

Summary of Background Data:

A meta-analysis of observed effects induced by nucleus pulposus reveals that these effects might relate to one specific cytokine, Tumor Necrosis Factor alpha (TNF(α).

Objectives.

To assess the presence of TNF(α) in pig nucleus pulposus cells and to see if blockage of TNF(α) also blocks the nucleus pulposus-induced reduction of nerve root conduction velocity.

Methods

Series-1: Cultured nucleus pulposus-cells were immunohistologically stained with a monoclonal antibody for TNF (α).

Series-2: Nucleus pulposus was harvested from lumbar discs and applied to the sacrococcygeal cauda equina in 13 pigs autologously. Four pigs received 100 mg of doxycycline intravenously, 5 pigs had a blocking monoclonal antibody to TNF-α applied locally in the nucleus pulposus, and 4 pigs remained non-treated and formed control. Three days after the application the nerve root conduction velocity was determined over the application zone by local electrical stimulation.

Results.

Series-1: TNF-α was found to be present in the nucleus pulposus-cells.

Series-2: The selective antibody to TNF-α limited the reduction of nerve conduction velocity, although not statistically significantly to the control series. However, treatment with doxycycline significantly blocked the nucleus pulposus-induced reduction of conduction velocity.

Conclusion.

For the first time a specific substance, Tumor Necrosis Factor-alpha, has been linked to the nucleus pulposus-induced effects of nerve roots after local application. Although the effects of this substance may be synergistic with other similar substances, the data of the present study may be of significant importance for the continued understanding of nucleus pulposus' biologic activity, and might also be of potential use for future treatment strategies of sciatica.

After previously being considered as just a biologically inactive tissue component compressing the spinal nerve root at disc herniation, the nucleus pulposus has recently been found to be highly active, inducing both structural and functional changes in adjacent nerve roots when applied epidurally (24, 37, 38, 41, 42). It has thereby been established that autologous nucleus pulposus may induce axonal changes and a characteristic myelin injury (24, 38, 41, 42), increased vascular permeability (9, 44), intra vascular coagulation (24, 36), and that membrane-bound structure or substances of the nucleus pulposus-cells are responsible for these effects (24, 37). The effects have also been found to be efficiently blocked by methyl-prednisolone and cyclosporin A (2,38). When critically looking at these data, one realizes that there is at least one cytokine that relates to all of these effects, Tumor Necrosis Factor alpha (TNF-α). To assess if TNF- may be involved in the nucleus pulposusinduced nerve root injury the presence of TNF-α in nucleus pulposus-cells was assessed and was studied if the nucleus pulposus-induced effects could be blocked by doxycycline and also by a selective monoclonal antibody.

Material and Methods

Series-1, Presence of TNF-α in pig nucleus pulposus-cells:

Nucleus pulposus (NP) from a total of 13 lumbar and thoracic discs were obtained from a pig used for other purposes. NP was washed once in Ham's F12 medium (Gibco BRL, Paisley, Scotland) and then centrifuged and suspended in 5 ml of collagenase solution in Ham's F12 medium (0.8 mg/inl, Sigma Chemical Co., St Louis, Mo., USA) for 40 minutes, at 37° C. in 25 cm2 tissue culture flasks. The separated NP-cell pellets were suspended in DMEM/F 12 1:1 medium (Gibco BRL, Paisley, Scotland) supplemented with 1% L-glutamine 200 mM (Gibco BRL, Paisley, Scotland), 50 µg/ml gentamycine sulphate (Gibco BRL, Paisley, Scotland) and 10% foetal calf serum (FCS), (Gibco BRL, Paisley, Scotland). The cells were cultured at 37° C. and 5% $CO_2$ in air for 3-4 weeks and then cultured directly on tissue culture treated glass slides (Becton Dickinson & Co Labware, Franklin Lakes, N.J., USA). After 5 days on the glass slides, the cells were fixed in situ by acetone for 10 minutes. After blocking irrelevant antigens by application of 3% $H_2O_2$ (Sigma Chemical Co., St Louis, Mo., USA) for 30 minutes and Horse Serum (ImmunoPure ABC, peroxidase mouse IgG staining kit nr.32028, Pierce, Rockford, Ill.) for 20 minutes, the primary antibody (Anti-pig TNF-α monoclonal purified antibody, Endogen, Cambridge, Mass., USA) was applied over night at +40° C., diluted at 1:10, 1:20 and 1:40. For control, BSA (bovine serum albumin, Intergen Co, New York, USA) suspended in PBS (phosphate buffered saline, Merck, Darmstadt, Germany) was applied in the same fashion. The next day the cells were washed with 1% BSA in PBS and the secondary antibody (ImmunoPure ABC, peroxidase mouse IgG staining kit nr.32028, Pierce, Rockford, Ill.) was applied for 30 minutes. To enhance this reaction, the cells were exposed to Avidin-Biotin complex for additionally 30 minutes (ImmunoPure ABC, peroxidase mouse IgG staining kit nr.32028, Pierce, Rockford, Ill.). The cells were then exposed to 20 mg of DAB (3,3-diaminobenzidine tetrahydrochloride nr. D-5905, Sigma Chemical Co., St Louis, Mo., USA) and 0.033 ml of 3% $H_2O_2$ in 10 ml of saline for 10 minutes. The cells were washed in PBS, dehydrated in a series of ethanol, mounted and examined by light microscopy by an unbiased observer regarding the presence of a brown colouration indicating presence of TNF-α.

Series-2, Neurophysiologic evaluation:

Thirteen pigs, (body weight 25-30 kg) received an intramuscular injection of 20 mg/kg body weight of Ketalar$^R$ (ketamine 50 mg/ml, Parke-Davis, Morris Plains, N.J.) and an intravenous injection of 4 mg/kg body weight of Hypnodil$^R$ (methomidate chloride 50 mg/ml, AB Leo, Helsingborg, Sweden) and 0. I mg/kg body weight of Stresnil$^R$ (azaperon 2 mg/ml, Janssen Pharmaceutica, Beerse, Belgium). Anaesthesia was maintained by additional intravenous injections of 2 mg/kg body weight of Hypnodil$^R$ and 0.05 mg/kg body weight of Stresnil$^R$. The pigs also received an intravenous injection of 0.1 mg/kg of Stesolid Novum$^R$ (Diazepam, Dumex, Helsingborg, Sweden) after surgery.

Nucleus pulposus was harvested from the 5th lumbar disc through a retro peritoneal approach (42). Approximately 40 mg of the nucleus pulposus was applied to the sacrococcygeal cauda equina through a midline incision and laminectomy of the first coccygeal vertebra. Four pigs did not receive any treatment (no treatment). Four other pigs received an intravenous infusion of 100 mg of doxycycline (Vibramycino, Pfizer Inc., New York, USA) in 100 ml of saline over 1 hour. In 5 pigs, the nucleus pulposus was mixed with 100 gl of a 1,11 mg/ml suspension of the anti-TNF-α antibody used in series 1, before application.

Three days after the application, the pigs were reanaesthetized by an intramuscular injection of 20 mg/kg body weight of Ketalar$^R$ and an intravenous injection of 35 mg/kg body weight of Pentothal$^R$ (Thiopental sodium, Abbott lab, Chicago, Ill.). The pigs were ventilated on a respirator. Anaesthesia was maintained by an intravenous bolus injection of 100 mg/kg body weight of Chloralose (α)-D(+)-gluco-chloralose, Merck, Darmstadt, Germany) and by a continuous supply of 30 mg/kg/hour of Chloralose. A laminectomy from the 4th sacral to the 3rd coccygeal vertebra was performed. The nerve roots were covered with Spongostane$^R$ (Ferrosan, Denmark). Local tissue temperature was continuously monitored and maintained at 37.5-38.0° C. by means of a heating lamp.

The cauda equina was stimulated by two E2 subdermal platinum needle electrodes (Grass Instrument Co., Quincy, Mass.) which were connected to a Grass SD9 stimulator (Grass Instrument Co., Quincy, Mass.) and gently placed intermittently on the cauda equina first 10 mm cranial and then 10 mm caudal to the exposed area. To ensure that only impulses from exposed nerve fibres were registered, the nerve root that exited from the spinal canal between the two stimulation sites were cut. An EMG was registered by two subdermal platinum needle electrodes which were placed into the paraspinal muscles in the tail approximately 10 mm apart. This procedure is reproducible and represents a functional measurement of the motor nerve fibres of the cauda equina nerve roots. The EMG was visualized using a Macintosh IIci computer provided with Superscope software and MacAdios II AID converter (GW Instruments, Sommerville, Mass.) together with a Grass P18 preamplifier (Grass Instrument Co., Quincy, Mass.). The separation distance between the first peaks of the EMG from the two recordings was determined and the separation distance between the two stimulation sites on the cauda equina was measured with calipers. The nerve conduction velocity between the two stimulation sites could thus be calculated from these two measurements. The person performing the neurophysiologic analyses was unaware of the experimental protocol for the individual animal, and after finishing the complete study the data were arranged in the three experimental groups and statistical differences between the groups were assessed by Student's t-test. The experimental protocol for this experiment was approved by the local animal research ethics committee.

Results

Series-1, Presence of TNF-α in pig nucleus pulposus-cells:

Examples of the light microscopic appearance of the stained glass slides. In the sections using BSA in PBS as "primary antibody" (control) no staining was observed, ensuring that there was no labelling and visualization of irrelevant antigens. When the anti-TNF-α antibody was applied at 1:40 dilution there was only a weak staining. However, the staining increased with diminishing dilutions of the antibody. The staining was seen in the soma of the cells and it was not possible to differentiate whether TNF-a was located in the cytoplasm, on the cell surface bound to the cell-membrane, or both.

Series-2, Neurophysiologic evaluation:

Application of non-modified nucleus pulposus and without any treatment induced a reduction in nerve conduction velocity similar to previous studies (no treatment, FIG. 2), whereas treatment with doxycycline completely blocked this reduction ($p<0.01$ Student's t-test). Local application of anti-TNF-α-antibody also induced a partial block of this reduction, although not as complete as doxycycline and not statistically significant to the no treatment-series.

Discussion

The data of the present study demonstrated that TNF-a may be found in nucleus pulposus-cells of the pig. If TNF-α was blocked by a locally applied selective monoclonal antibody, the nucleus pulposus-induced reduction of nerve root conduction velocity was partially blocked, although no statistically significant compared to the series with non-treated animals. However, if doxycycline was used to inhibit TNF-α, the reduction of nerve conduction velocity was significantly blocked.

In recent years, it has been verified that local application of autologous nucleus pulposus may injure the adjacent nerve roots. Thus, it has become evident that the nerve root injury seen at disc herniation may not be solely based on mechanical deformation of the nerve root, but may also be induced by unknown "biochemical effects" related to the epidural presence of herniated nucleus pulposus. Although this new research field has generated many experimental studies, the echanisms and substances involved are not fully known. It has been seen that local application of autologous nucleus pulposus may induce axonal injury (24, 37,38, 40-42), a characteristic injury of the myelin sheath (24,38, 40-42), a local increase of vascular permeability (9, 36, 44), intra vascular coagulations, reduction of intra neural blood flow (43), and leukotaxis (36). It has been seen that the nucleus pulposus-related effects may be blocked efficiently by methylprednisolone (38) and cyclosporin A (2), and slightly less efficiently by indomethacin (3), and lidocaine (69). Further, it has been understood that the effects are mediated by the nucleus pulposus-cells (37), particularly by substances or structures bound to the cell-membranes (25). When critically considering these data, it becomes evident that at least one specific cytokine could be related to these observed effects, Tumor Necrosis Factor-alpha (TNF-α). TNF-α may induce nerve injury (29, 31, 45, 50, 66) mainly seen as a characteristic myelin injury that closely resembles the nucleus pulposus-induced myelin-injury (29, 47, 51, 54, 62, 64, 66, 70). TNF-α may also induce an increase in vascular permeability (47, 66) and initiate coagulation (22, 34, 63). Further, TNF-α may be blocked by steroids (4, 8, 21, 61, 68), and cyclosporin A (11, 55, 67, 68). However, the blocking effect on TNF-α is not so pronounced by NSAID (14, 17, 20) and very low or the opposite by lidocaine (5, 32, 46, 60). It was recently observed that local application of nucleus pulposus may induce pain-related behaviour in rats, particularly thermal hyperalgesia (23, 40). TNF-α has also been found to be related to such pain-behaviouristic changes (12, 35, 56, 66), and also to neuropathies in general (30, 54, 56, 57). However there are no studies that have assessed the possible presence of TNF-α in the cells of the nucleus pulposus.

To assess if TNF-α could be related to the observed nucleus pulposus induced reduction in nerve root conduction velocity it was necessary first to analyse if there was TNF-α in the nucleus pulposus-cells. The data clearly demonstrated that TNF-a was present in these cells. TNF-α is produced as precursor (pro-TNF) that is bound to the membrane and it is activated by cleavage from the cell-membrane by a zinc-dependent metallo-endopeptidase (TNF-alpha converting enzyme, TACE) (6, 15, 16, 48, 49). This may thus relate well to experimental findings where application of the mere cell-membranes of autologous nucleus pulposus-cells induced nerve conduction velocity reduction, which indicated that the effects were mediated by a membrane-bound substances. Second, the effects of the TNF-α had to be blocked in a controlled manner. We then first choose to add the same selective antibody that was used for immunohistochemistry in series 1, which is known to also block the effects of TNF-α, to the nucleus pulposus before application. Also, we choose to treat the pigs with doxycycline, which is known to block TNF-α (26, 27, 33, 52, 53). However, due to the low pH of the doxycycline preparation it was chosen to treat the pigs by intravenous injection instead of local addition to the nucleus pulposus since nucleus pulposus at a low pH has been found to potentiate the effects of the nucleus pulposus (38, 39).

The data regarding nerve conduction velocity showed that the reduction was completely blocked by the systemic-treatment and that the nerve conduction velocities in these series was close to the conduction velocity after application of a control substance (retro peritoneal fat) from a previous study (42). Application of the anti-TNF-α-antibody to the nucleus pulposus also partially prevented the reduction in nerve conduction velocity, however, not as pronounced as doxycycline, and the velocity in this series was not statistically different to the velocity in the series with not treated animals, due to the wide deviation of the data.

The fact that the local anti-TNF-α antibody treatment only partially blocked the nucleus pulposus-induced reduction of nerve conduction velocity and the high standard deviation of the data could probably have at least three different explanations. First, if looking at the specific data within this group it was found that the nerve conduction velocity was low in 2 animals (mean 37.5 m/s) and high in 3 animals (mean 81.3 m/s). There are thus 2 groups of distinctly different data within the anti-TNF-α treatment series. This will account for the high standard deviation and might imply that the blocking effect was sufficient in 3 animals and non-sufficient in 2 animals. The lack of effects in these animals could be based simply on the amount of antibodies in relation to TNF-α molecules not being sufficient, and if a higher dose of the antibody had been used, the TNF-α effects would thus have been blocked even in these animals. Such a scenario could then theoretically imply that TNF-α alone is responsible for the observed nucleus pulposus-induced effects, and that this could not be verified experimentally due to the amount of antibody being too low.

Second, it is also known that tetracyclines such as doxycycline and minocycline may block a number of cytokines and other substances. For instance they may block IL-1 (1, 28, 58), IFNγ(27), NO-synthetaseI, and metalloproteinases (1, 53, 58). Particularly IL-1 and IFNγ are known to act synergistically with TNF-α and are known to be more or less neurotoxic (7, 10, 13, 18, 19, 56, 59). These substances are also blocked by steroids and cyclosporin A which corresponds well with the previous observations on nucleus pulposus-induced nerve root injury which have shown that the nucleus pulposus-induced effects may be blocked by these substances (8, 67). One may therefore also consider the possibility that a selective block of TNF-α may not be sufficient to completely block the nucleus pulposus-induced effects on nerve function, and that simultaneous block of other synergistic substances is necessary as well. Thus, this scenario, on the other hand, implies that TNF-α is not solely responsible for the nucleus pulposus-induced effects, and that other synergistic substances, which are also blocked by doxycycline, may be necessary.

TNF-α may have various pathophysiologic effects. It may have direct effects on tissues such as nerve tissue and blood vessels, it may trigger other cells to produce other pathogenic substances and it may trigger release of more TNF-α both by inflammatory cells and also by Schwann-cells locally in the nerve tissue (65). ]here is thus reason to believe that even low amounts of TNF-α may be sufficient to initiate these processes and that there is a local recruitment of cytokine producing cells and a subsequent increase in production and release of other cytokines as well as TNF-α. TNF-α may therefore act as the "ignition key" of the pathophysiologic processes and play an important role for the initiation of the pathophysiologic cascade behind the nucleus pulposus-induced nerve injury.

In conclusion, although the exact role of TNF-α can not be fully understood from the experimental set-up, we may conclude that for the first time a specific substance (TNF-a) has been linked to the nucleus pulposus-induced nerve root injury, probably potentiated by other substances which are also blocked by doxycycline, such as for instance IL1, IFNγ and NO-synthetase. This new information may be of significant importance for the continued understanding of nucleus pulposus-induced nerve injury as well as raising the question of the potential future clinical use of pharmacological interference with TNF-α and related substances, by for instance doxycycline or metalloproteinase-inhibitors, for the treatment of sciatica.

The presence of TNF-α in pig nucleus pulposus-cells was thus immunohistochemically verified. Block of TNF-α by a monoclonal antibody partially limited the nucleus pulposus-induced reduction of nerve root conduction velocity, whereas intravenous treatment with doxycycline significantly blocked this reduction. These data for the first time links one specific substance, TNF-α, to the nucleus pulposusinduced nerve injury.

Aminoguanidine has showed to inhibit the release of nitrogen oxide (NO) at nerve root injuries by inhibiting inducible nitrogen oxide synthetase, and aminoguanidine is thus one compound that inhibits a compound trigged by the release of TNF-α.

The compounds of the invention can be administered in a variety of dosage forms, e.g., orally, in the form of tablets, capsules, sugar or film coated tablets, liquid solutions; rectally, in the form of suppositories; parenterally, e.g., intramuscularly or by intravenous injection or infusion. The therapeutic regimen for the different clinical syndromes must be adapted to the type of pathology taken in to account, as usual, also the route of administration, the form in which the compound is administered and age, weight, and condition of the subject involved.

The oral route is employed, in general, for all conditions, requiring such compounds. In emergency cases preference is given to intravenous injection. For these purposes the compounds of the invention can be administered orally at doses ranging from about 20 to about 1500 mg/day. Of course, these dosage regimens may be adjusted to provide the optimal therapeutic response.

The nature of the pharmaceutical composition containing the compounds of the invention in association with pharmaceutically acceptable carriers or diluents will, of course, depend upon the desired route of administration. The composition may be formulated in the Conventional manner with the usual ingredients. For example, the compounds of the invention may be administered in the form of aqueous or oily solutions or suspensions, tablets, pills, gelatine capsules (hard or soft ones) syrups, drops or suppositories.

Thus for oral administration, the pharmaceutical compositions containing the compounds of the invention are preferably tablets, pills or gelatine capsules, which contain the active substance together with diluents, such as lactose, dextrose, sucrose, mannitol, sorbitol, cellulose; lubricants, e.g., silica, talc, stearic acid, magnesium or calcium stearate, and/or polyethylene glycols; or they may also contain binders, such as starches, gelatine, methyl cellulose, carboxymethylcellulose, gum arabic, tragacanth, polyvinylpyrrolidone; disaggregating agents such as starches, alginic acid, alginates, sodium starch glycolate, microcrystalline cellulose; effervescing agents such a carbonates and acids; dyestoffs; sweeteners; wetting agents, such as lecithin, polysorbates, laurylsulphates; and in general non-toxic and pharmaceutically inert substances used in the formulation of pharmaceutical compositions. Said pharmaceutical compositions may be manufactured in known manners, e.g., by means of mixing, granulating, tableting, sugar-coating or film-coating processes. In the case film providing compounds can be selected to provide release in the right place in the intestinal tract with regard to absorption and maximum effect. Thus pH-dependent film formers can be used to allow absorption in the intestines as such, whereby different phthalate are normally used or acrylic acid/methacrylic acid derivatives and polymers.

The liquid dispersions for oral administration may be e.g., syrups, emulsion, and suspensions.

The syrups may contain as carrier, e.g., saccharose, or saccharose with glycerine and/or mannitol and/or sorbitol.

Suspensions and emulsions may contain as carrier, e.g., a natural gum, such as gum arabic, xanthan gum, agar, sodium alginate, pectin, methyl cellulose, carboxymethylcellulose, polyvinyl alcohol.

The suspension or solutions for intramuscular injections may contain together with the active compound, a pharmaceutically acceptable carrier, such as e.g., sterile water, olive oil, ethyl oleate, glycols, e.g., propylene glycol, and if so desired, a suitable amount of lidocaine hydrochloride. Adjuvants for trigging the injection effect can be added as well.

The solutions for intravenous injection or infusion may contain as carrier, e.g., sterile water, or preferably, a sterile isotonic saline solution, as well as adjuvants used in the field of injection of active compounds.

The suppositories may contain together with the active compound, a pharmaceutically acceptable carrier, e.g., cocoa-butter polyethylene glycol, a polyethylene sorbitan fatty acid ester surfactant or lecithin.

REFERENCES

1. Amin A R, Attur M G, Thakker G D, Patel P D, Vyas P R, Patel R N, Patel I R, Abramson S B. A novel mechanism of action of tetracyclines: effects on nitric oxide syntheses. *Proc Natl Acad Sci USA* 1996; 93:14014-9.
2. Arai I, Konno S, Otani K, Kikuchi S, Olmarker K. Cyclosporin A blocks the toxic effects of nucleus pulposus on spinal nerve roots. Manuscript
3. Arai I, Mao G P, Otani K, Konno S, Kikuchi S, Olmarker K. Indomethacin blocks nucleus pulposus related effects in adjacent nerve roots. Manuscript
4. Baumgartner R A, Deramo V A, Beaven M A. Constitutive and inducible mechanisms for synthesis and release of cytokines in immune cell lines. *J Immunol* 1996; 157: 4087-93.
5. Bidani A, Heming T A. Effects of lidocaine on cytosolic pH regulation and stimulus-induced effector functions in alveolar macrophages. *Lung* 1997; 175:349-61.
6. Black R A, Rauch C T, Kozlosky C J, Peschon J J, Slack J L, Wolfson M F, Castner B J, Stocking K L, Reddy P, Srinivasan S, Nelson N, Boiani N, Schooley K A, Gerhart M, Davis R, Fitzner J N, Johnson R S, Paxton R J, March C J, Cerretti D P. A metalloproteinase disintegrin that releases tumour-necrosis factor-a from cells. *Nature* 1997; 385:729-33.
7. Bluthe R M, Dantzer R, Kelley K W. Interleukin-1 mediates behavioural but not metabolic effects of tumor necrosis factor alpha in mice. *Eur J Pharmacol* 1991; 209:281-3.
8. Brattsand R, Linden M. Cytokine modulation by glucocorticoids: mechanisms and actions in cellular studies. *Aliment Pharmacol Ther* 1996; 10:81-90.
9. Byrod G, Otani K, Rydevik B, Olmarker K. Acute increase in endoneural vascular permeability induce by epidural application of nucleus pulposus on spinal nerve roots. Manuscript
10. Chao C C, Hu S, Ehrlich L, Peterson P K. Interleukin-1 and tumor necrosis factor-alpha synergistically mediate neurotoxicity: involvement of nitric oxide and of N-methyl-D-aspartate receptors. *Brain Behav Immun* 1995; 9:355-65.
11. Dawson J, Hurtenbach U, MacKenzie A. Cyclosporin A inhibits the in vivo production of interleukin-Ibeta and tumour necrosis factor alpha, but not interleukin-6, by a T-cellindependent mechanism. *Cytokine* 1996; 8:882-8.
12. DeLeo J A, Colburn R W, Rickman A J. Cytokine and growth factor immunohistochemical spinal profiles in two animal models of mononeuropathy. *Brain Res* 1997; 759: 50-7.
13. Gadient R A, Cron K C, Often U. Interleukin-1 beta and tumor necrosis factor-alpha synergistically stimulate nerve growth factor (NGF) release from cultured rat astrocytes. *Neurosci Lett* 1990; 117:335-40.
14. Garcia-Vicuna R, Diaz-Gonzalez F, Gonzalez-Alvaro 1, del Pozo M A, Moilinedo F, Cabanas C, Gonzalez-Amaro R, Sanchez-Madrid F. Prevention of cytokine-induced changes in leucocyte adhesion receptors by nonsteroidal antiinflammatory drugs from the oxicam family. *Arthritis Rheum* 1997; 40:143-53.
15. Gearing A J, Beckett P, Christodoulou M, Churchill M, Clements J, Davidson A H, Drummond A H, Galloway W A, Gilbert R, Gordon J L, et al. Processing of tumour necrosis factor-alpha precursor by metalloproteinases. *Nature* 1994; 370:555-7.
16. Gazelle E, Banda M J, Leppert D. Matrix metallo-proteinases in immunity. *J Immunol* 1996; 156: 14.
17. Gonzalez E, de la Cruz C, de Nicolas R, Egido J, Herrero-Beaumont G. Long-term effect of nonsteroidal anti-inflammatory drugs on the production of cytokines and other inflammatory mediators by blood cells of patients with osteosis. *Agents Actions* 1994; 41:171-8.
18. Hartung H P, Jung S, Stoll G, Zielasek J, Schmidt B, Archelos J J, Toyka K V. Inflammatory mediators in demyelinating disorders of the CNS and PNS. *J Neuroinununol* 992; 40:197-210.
19. Hattori A, Iwasald S, Murase K, Tsujimoto M, Sato M, Hayashi K, Kohno M. Tumor necrosis factor is markedly synergistic with interleukin I and ii3terferon-gamma in stimulating the production of nerve growth factor in fibroblasts. *FEBS Lett* 1994; 340:177-80.
20. Herman J H, Sowder W G, Hess B Y. Nonsteroidal anti-inflammatory drug modulation of prosthesis pseudomembrane induced bone resorption. *J Rheunutol* 1994; 21:338-43.
21. Iwamoto S, Takeda K. [Possible cytotoxic mechanisms of TNF in vitro]. *Hum Cell* 1990; 3:107-12.
22. Jurd K M, Stephens C J, Black M M, Hunt B J. Endothelial cell activation in cutaneous vasculitis. *Clin Exp Dermatol* 1996; 21:28-32.
23. Kawakami M, Tamaki T, Weinstein J N, Hashizume H, Nishi H, Meller S T. Pathomechanism of pain-related behaviour produced by allografts of intervertebral disc in the rat. *Spine* 1996; 21:2101-7.
24. Kayama S, Konno S, Olmarker K, Yabuki S, Kikuchi S. Incision of the anulus fibrosis induces nerve root morphologic, vascular, and functional changes. An experimental study. *Shine* 1996; 21:2539-43.
25. Kayama S, Olmarker K, Larsson K, Sj6gren-Jansson E, Lindahl A, Rydevik B. Cultured, autologous nucleus pulposus cells induce structural and functional changes in spinal nerve roots. Manuscript
26. Kloppenburg M, B-an B M, de Rooij-Dijk H H, Miltenburg A M, Daha M R, Breedveld F C, Dijkmans B A, Verweij C. The tetracycline derivative minocycline differentially affects cytokine production by monocytes and T lymphocytes. *Antimicrob Agents Chemother* 1996; 40:934-40.
27. Kloppenburg M, Verweij C L, Miltenburg A M, Verboeven A J, Daha M R, Dijkmans B A, Breeveld F C. The influence of tetracyclines on T cell activation. *Clin Exp Immunol* 1995; 102:635-41
28. Lamster I B, Pullman J R, Celenti R S, Grbic J T. The effect of tetracycline fiber therapy on beta-glucuronidase and interleukin-1 beta in crevicular fluid. *J Clin Periodontol* 1996; 23:816-22.
29. Liberski P P, Yanagihara R, Nerurkar V, Gajdusek D C. Further ultrastructural studies of lesions induced in the optic nerve by tumor necrosis factor alpha (TNF-alpha): a 30. Lin X H, Kashima Y, Khan M, Heller K B, Gu X Z, Sadun A A. An immunohistochemical study of TNF-a in optic nerves from AIDS patients. *Curr Eve Res* 1997; 16:1064-8.
31. Madigan M C, Sadun A A, Rao N S, Dugel P U, Tenhula W N, Gill P S. Tumor necrosis factor-alpha (TNF-alpha)-induced optic neuropathy in rabbits. *Neurol Res* 1996; 18:176-84.
32. Matsumori A, Ono K, Nishio R, Nose Y, Sasayama S. Amiodarone inhibits production of tumor necrosis factor-alpha by human mononuclear cells: a possible mechanism for its effect in heart failure. *Circulation* 1997; 96:1386-9.
33. Milano S, Arcoleo F, D'Agostino P, Cillari E. Intraperitoneal injection of tetracyclines protects mice from lethal endotoxemia downregulating inducible nitric oxide synthase in various organs and cytokine and nitrate secretion in blood. *Antimicrob Agents Chemother* 1997; 41:117-21.
34. Nawroth P, Handley D, Matsueda G, De Waal R, Gerlach H, Blohm D, Stem D. Tumor necrosis factor/cachectin-induced intra vascular fibrin formation in meth A fibrosarcomas. *J Exp Med* 1988; 168:637-47.
35. Oka T, Wakugawa Y, Hosoi M, Oka K, Hori T. Intracerebroventricular injection of tumor necrosis factor-alpha induces thermal hyperalgesia in rats. *Neuroimmunomodulation* 1996; 3:135-40.
36. Olmarker K, Blomquist J, Stromberg J, Nannmark, U, Thomsen P, Rydevik B. Inflamma-togenic properties of nucleus pulposus. *Spine* 1995; 20:665-9.
37. Olmarker K, Brisby H, Yabuki S, Nordborg C, Rydevik B. The effects of normal, frozen, and hyaluronidase-digested nucleus pulposus on nerve root structure and function. *Spine* 1997; 22:4715; discussion 476.
38. Olmarker K, Byrod G, Comefjord M, Nordborg C, Rydevik B. Effects of methylprednisolone on nucleus pulposus-induced nerve root injury. *Spine* 1994; 19:1803-8.
39. Olmarker K, lwabuchi M, Larsson K, Rydevik B. Effects of in vitro degenerated nucleus pulposus on nerve root conduction velocity. Manuscript
40. Olmarker K, Myers R R. Pathogenesis of sciatic pain: Role of herniated nucleus pulposus and deformation of spinal nerve root and DRG. Manuscript
41. Olmarker K, Nordborg C, Larsson K, Rydevik B. Ultrastructural changes in spinal nerve roots induced by autologous nucleus pulposus. *Spine* 1996; 21:411-4.
42. Olmarker K, Rydevik B, Nordborg C. Autologous nucleus pulposus induces neurophysiologic and histologic changes in porcine cauda equina nerve roots [see comments]. *Spine* 1993; 18:1425-32.
43. Otani K, Arai I, Mao G P, Konno S, Olmarker K, Kikuchi S, Nucleus pulposus-induced nerve root injury. The relationship between blood flow and nerve conduction velocity. Manuscript
44. Otani K, Mao G P, Arai I, Konno S, Olmarker K, Kikuchi S, Nucleus pulposus-induced increase in vascular permeability in the nerve root. Manuscript
45. Petrovich M S, Hsu H Y, Gu X, Dugal P, Heller K B, Sadun A A. Pentoxifylline suppression of TNF-alpha mediated axonal degeneration in the rabbit optic nerve. *Neurol Res* 1997; 19:551-4.
46. Pichler W J, Zanni M, von Greyerz S, Schnyder B, Mauri-HeUweg D, Wendland, T. High IL-5 production by human drug-specific T cell clones. *Int Arch Allergy Immunol* 1997; 113 177-80.
47. Redford E J, Hall S M, Smith K J. Vascular changes and demyelination induced by the intra neural injection of tumour necrosis factor. *Brain* 1995; 118:869-78.
48. Robache-Gallea S, Bruneau J M, Robbe H, Morand V, Capdevila C, Bhatnagar N, Chouaib S, Roman-Roman S. Partial purification and characterization of a tumor necrosis factor-alpha converting activity. *Eur J Immunol* 1997; 27:1275-82.
49. Rosendahl M S, Ko S C, Long D L, Brewer M T, Rosenzweig B, Hedl E, Anderson L, Pyle S M, Moreland J, Meyers M A, Kohno T, Lyons D, Lichenstein H S. Identification and characterization of a pro-tumor necrosis factor-alpha-processing enzyme from the ADAM family of zinc metalloproteases. *J Biol Chem* 1997; 272:24588-93.
50. Said G, Hontebeyrie-Joskowicz M. Nerve lesions induced by macrophage activation. *Res Immunol* 1992; 143:589-99.
51. Sehnaj K W, Raine C S. Tumor necrosis factor mediates myelin and ligodendrocyte damage in vitro. *Ann Neurol* 1988; 23:339-46.
52. Shapira L, Houri Y, Barak V, Halabi A, Soskoine W A, Stabholz A. Human monocyte response to cementum extracts from periodontally diseased teeth: effect of conditioning with tetracycline. *J Periodontol* 1996; 67:682-7.
53. Shapira L, Houri Y, Barak V, Soskolne W A, Halabi A, Stabholz A. Tetracycline inhibits' Porphyromonas gingivalis lipopolysaccharide-induced lesions in vivo and TNF a processing in vitro. *J Periodontal Res* 1997; 32:183-8.
54. Sharief M K, Ingram D A, Swash M. Circulating tumor necrosis factor-alpha correlates with electrodiagnostic abnormalities in Guillain-Barre syndrome. *Ann Neurol* 1997; 42:68-2073.
55. Smith C S, Ortega G, Parker L, Shearer W T. Cyclosporin A blocks induction of tumor necrosis factor-alpha in human B lymphocytes. *Biochem Biophys Res Commun* 1994; 204:383-90.
56. Sonuner C, Schmidt C, George A, Toyka K V. A metalloprotease-inhibitor reduces pain associated behaviour in mice with experimental neuropathy. *Neurosci Lett* 1997; 237:45-8.
57. Sorkin L S, Xiao W H, Wagner R, Myers R R. Tumour necrosis factor-alpha induces ectopic activity in nociceptive primary afferent fibres. *Neuroscience* 1997; 81:255-62.
58. Steinmeyer J, Daufeldt S, Taiwo Y O. Pharmacological effect of tetracyclines on proteoglycanases from interleukin-1-treated articular cartilage. *Biochem Pharmacol* 1998; 55:93-100.
59. Stoll G, Jung S, Jander S, van der Meide P, Hartung H P. Tumor necrosis factor-alpha in immunomediated demyelination and Wallerian degeneration of the rat peripheral nervous system. *Neuroimmunol* 1993; 45:175-82.
60. Takao Y, Mikawa K, Nishina K, Maekawa N, Obara H. Lidocaine attenuates hyperoxic lung injury in rabbits. *Acta Anaesthesiol Scand* 1996; 40:318-25.
61. Teoh K H, Bradley C A, Galt J, Burrows H. Steroid inhibition of cytokine-mediated vasodilation after warm heart surgery. *Circulation* 1995; 92:II347-53.
62. Tsukamoto T, Ishikawa M, Yamamoto T. Suppressive effects of TNF-a on myelin formation in vitro. *Acta Neurol Scand* 1995; 91:71-5.
63. van der Poll T, Jansen P M, Van Zee K J, Welborn M Br, de Jong I, Hack C E, Loetscher H, Lesslauer W, Lowry S F, Moidawer L L. Tumor necrosis factor-alpha induces activation of coagulation and fibrinolysis in baboons through an exclusive effect on the p55 receptor. *Blood* 1996; 88:922-7.
64. Villarroya H, Violleau K, Ben Younes-Chennoufi A, Baumann N. Myelin-induced experimental allergic encephalomyelitis in Lewis rats: tumor necrosis factor alpha levels in serum of cerebrospinal fluid immunohistochemical expression in glial cells and neurophages of optic nerve and spinal cord. *J Neuroimmunol* 1996; 64:55-61.
65. Wagner R, Myers R R. Schwann cells produce tumor necrosis factor alpha: expression in injured non-injured nerves. *Neuroscience* 1996; 73:625-9.
66. Wagner R, Myers R R. Endoneurial injection of TNF-a produces neuropathic pain behaviours. *Neurorgport* 1996; 7:2897-901.
67. i S, Sakaida I, Uchida K, Kiinura T, Kayano K, Okita K. Preventive effect of cyclosporin A on experimentally induced acute liver injury in rats. *Liver* 1997; 17:107-14.
68. Wershil B K, Furuta G T, Lavigne J A, Choudhury A R, Wang Z S, Galli S J. Dexamethasone cyclosporin A suppress mast cell-leukocyte cytokine cascades by multiple mechanisms. Int *Arch Allergy Immunol* 1995; 107:323-4.
69. Yabuki S, Kawaguchi Y, Olmarker K, Rydevik B. Effects of lidocaine on nucleus pulposus-induced nerve root injury. Manuscript
70. Zhu J, Bai X F, Mix E, Link H. Cytokine dichotomy in peripheral nervous system influences the outcome of experimental allergic neuritis: dynamics of mRNA expression for IL-1 beta, IL-6, IL-10, IL-12, TNF-a, TNF-beta, and cytolysin. *Clin Immunol Immunopathol* 1997; 84:85-94.

The invention claimed is:

1. A method of treating or alleviating one or more symptoms of a spinal disorder mediated by nucleus pulposus, which spinal disorder is not arthritis or a related inflammatory disorder, said method comprising the step of administering a therapeutically active amount of one or more TNF-α inhibitors selected from the group consisting of a soluble cytokine receptor and a TNF-α blocking antibody to a patient in need of said treatment.

2. The method of claim 1, wherein the spinal disorder involves one or more symptoms of pain.

3. The method of claim 1, wherein the spinal disorder is a disc disorder.

4. The method of claim 1, wherein the spinal disorder is a disorder of vertebral bone.

5. The method of claim 1, wherein the spinal disorder involves structural or functional damage to nerves.

6. The method of claim 5, wherein the spinal disorder involves structural or functional damage to nerves which are situated close to a disc and/or to nucleus pulposus.

7. The method of claim 1, wherein the spinal disorder involves mechanical deformation of a nerve.

8. The method of claim 1, wherein the spinal disorder involves reduced nerve root conduction.

9. The method of claim 1, wherein said spinal disorder is caused by a disc herniation.

10. The method of claim 1, wherein said spinal disorder is sciatica.

11. The method of claim 1, wherein the TNF-α inhibitor is a soluble cytokine receptor.

12. The method of claim 1, wherein the TNF-α inhibitor is an antibody.

13. The method of claim 1, wherein the TNF-α inhibitor is administered locally.

14. The method of claim 1, wherein the TNF-α inhibitor is administered parenterally.

15. The method of claim 14, wherein the TNF-α inhibitor is administered via intramuscular (i.m.), or intravenous (I.V.) injection.

16. A method of treating or alleviating one or more symptoms of a spinal disorder mediated by nucleus pulposus, which spinal disorder is not arthritis or a related inflammatory disorder, and wherein the spinal disorder is a nucleus pulposus induced nerve injury, said method comprising the step of administering a therapeutically active amount of one or more TNF-α inhibitors selected from the group consisting of a soluble cytokine receptor and a TNF-α blocking antibody to a patient in need of said treatment.

17. The method of claim 16, wherein the spinal disorder involves a herniated disc or sciatica.

18. The method of claim 16, wherein the TNF-α inhibitor is an antibody.

19. The method claim 18, wherein the antibody is a monoclonal antibody.

20. The method of claim 19, wherein the monoclonal antibody is selective for TNF-α.

21. The method of claim 16, wherein the TNF-α inhibitor is a soluble cytokine receptor.

22. The method of claim 18 or 21, wherein the TNF-α inhibitor is administered locally.

23. The method of claim 18 or 21, wherein the TNF-α inhibitor is administered parenterally.

24. The method of claim 1 or 16, wherein the TNF-α inhibitor is administered in a pharmaceutical composition comprising a pharmaceutically acceptable carrier.

25. The method of claim 24, wherein the pharmaceutical composition is a liquid solution, an emulsion, or a suspension.

26. The method of claim 24, wherein the pharmaceutical composition comprises a carrier selected from gum arabic, xanthan gum, agar, sodium alginate, pectin, methylcellulose, carboxymethylcellulose, polyvinylalcohol, ethyl oleate, a glycol, a polyethylene sorbitan fatty acid ester surfactant, or lecithin.

27. The method of claim 24, wherein the pharmaceutical composition comprises lidocaine hydrochloride.

28. A method for treating or alleviating one or more symptoms of a disc herniation in a patient, the method comprising administering a therapeutically active amount of a pharmaceutical composition comprising a TNF-α inhibitor selected from the group consisting of a soluble cytokine receptor and a TNF-α blocking antibody and a pharmaceutically acceptable carrier to a patient exhibiting one or more symptoms of a disc herniation.

29. A method for treating or alleviating one or more symptoms of sciatica in a patient, comprising administering a therapeutically active amount of a pharmaceutical composition comprising a TNF-α inhibitor selected from the group consisting of a soluble cytokine receptor and a TNF-α blocking antibody and a pharmaceutically acceptable carrier to a patient exhibiting one or more symptoms of sciatica.

30. The method of claim 28 or 29, wherein the one or more symptoms of disc herniation or sciatica include symptoms of pain.

31. The method of claim 28 or 29, wherein the pharmaceutical composition is administered locally.

32. The method of claim 28 or 29, wherein the pharmaceutical composition is administered parenterally.

33. The method of claim 28 or 29, wherein the pharmaceutical composition is a liquid solution, an emulsion, or a suspension.

34. The method of claim 28 or 29, wherein the pharmaceutical composition comprises a carrier selected from gum arabic, xanthan gum, agar, sodium alginate, pectin, methylcellulose, carboxymethylcellulose, polyvinylalcohol, ethyl oleate, a glycol, a polyethylene sorbitan fatty acid ester surfactant, or lecithin.

35. The method of claim 28 or 29, wherein the TNF-α inhibitor is a soluble cytokine receptor.

36. The method of claim 28 or 29, wherein the TNF-α inhibitor is an antibody.

37. The method of claim 36, wherein the antibody is a monoclonal antibody.

38. The method of claim 37, wherein the monoclonal antibody is selective for TNF-α.

39. A method of treating or alleviating one or more symptoms of a spinal disorder mediated by nucleus pulposus, which spinal disorder is not arthritis or a related inflammatory disorder, said method comprising the step of administering a therapeutically active amount of one or more TNF-α inhibitors that selectively block TNF-α to a patient in need of said treatment.

40. The method of claim 39, wherein the one or more TNF-α inhibitors is administered locally to the spinal disorder.

41. The method of claim 39, wherein at least one of the one or more TNF-α inhibitors is an antibody.

42. The method of claim 41, wherein the antibody is a monoclonal antibody.

43. The method of claim 39, wherein at least one of the one or more TNF-α inhibitors is a soluble cytokine receptor.

44. The method of claim 39, wherein the spinal disorder involves a herniated disc or sciatica.

45. The method of claim 1, wherein the TNF-α inhibitor is administered epidurally.

46. The method of claim 12, wherein the antibody is a monoclonal antibody.

47. The method of claim 46, wherein the monoclonal antibody is selective for TNF-α.

48. The method of claim 16, wherein the TNF-α inhibitor is administered epidurally.

49. The method of claim 28 or 29, wherein the TNF-α inhibitor is administered epidurally.

50. The method of claim 42, wherein the monoclonal antibody is selective for TNF-α.

51. The method of claim 39, wherein the TNF-α inhibitor is administered epidurally.

\* \* \* \* \*

UNITED STATES PATENT AND TRADEMARK OFFICE
CERTIFICATE OF CORRECTION

| | | |
|---|---|---|
| PATENT NO. | : 7,811,990 B2 | |
| APPLICATION NO. | : 11/788651 | |
| DATED | : October 12, 2010 | |
| INVENTOR(S) | : Kjell Olmarker and Bjorn Rydevik | |

It is certified that error appears in the above-identified patent and that said Letters Patent is hereby corrected as shown below:

Title Page, Title (54), after "RECEPTORS" please insert --AND--;

Column 1, line 1, after "RECEPTORS" please insert --AND--;

Column 13, line 50 (Claim 9), please delete "said" and insert --the-- therefor;

Column 13, line 52 (Claim 10), please delete "said" and insert --the-- therefor;

Column 14, line 11 (Claim 19), after "method" please insert --of--.

Signed and Sealed this
Sixteenth Day of August, 2011

David J. Kappos
*Director of the United States Patent and Trademark Office*